(12) United States Patent
Holmström et al.

(10) Patent No.: US 8,321,016 B2
(45) Date of Patent: Nov. 27, 2012

(54) IMPLANTABLE MEDICAL DEVICE AND A METHOD COMPRISING MEANS FOR DETECTING AND CLASSIFYING VENTRICULAR TACHYARRHYTHMIAS

(75) Inventors: Nils Holmström, Järfälla (SE); Andreas Blomqvist, Spånga (SE); Sven-Erik Hedberg, Kungsängen (SE); Malin Öhlander, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 454 days.

(21) Appl. No.: 12/602,533

(22) PCT Filed: Jun. 13, 2007

(86) PCT No.: PCT/SE2007/000581
§ 371 (c)(1),
(2), (4) Date: Dec. 1, 2009

(87) PCT Pub. No.: WO2008/153450
PCT Pub. Date: Dec. 18, 2008

(65) Prior Publication Data
US 2010/0179411 A1   Jul. 15, 2010

(51) Int. Cl.
*A61N 1/365* (2006.01)
*A61N 1/37* (2006.01)

(52) U.S. Cl. .......................... 607/14; 607/18

(58) Field of Classification Search .................. 607/5–7, 607/14, 17, 18, 28
See application file for complete search history.

(56) References Cited

U.S. PATENT DOCUMENTS

| 5,311,874 A | 5/1994 | Baumann et al. |
|---|---|---|
| 5,545,186 A | 8/1996 | Olson et al. |
| 7,376,463 B2 * | 5/2008 | Salo et al. ...................... 607/17 |
| 7,904,158 B2 * | 3/2011 | Stegemann et al. ............ 607/18 |
| 2005/0154421 A1 | 7/2005 | Ousdigian |
| 2006/0041280 A1 * | 2/2006 | Stahmann et al. .............. 607/17 |
| 2007/0043394 A1 | 2/2007 | Zhang et al. |
| 2007/0078356 A1 | 4/2007 | Faber et al. |

OTHER PUBLICATIONS

"The Transthoracic Impedance Cardiogram is a Potential Haemodynamic Sensor for an Automated External Defibrillator," Johnston, et al., European Heart Journal, No. 19 (1998) pp. 1879-1888.
"Does Transcardiac Impedance Reflect Haemodynamic Status in the Canine Model with Twelve-Month Chronically Implanted Defibrillation Patches?," Weiss et al, European Journal of Cardiac Pacing and Electrophysiology, vol. 3, No. 1 (1993) pp. 50-58.
"Mixed Venous Oxygen Saturation for Differentiating Stable From Unstable Tachycardias," Cohen et al, American Heart Journal, vol. 122, No. 3 (1991), pp. 733-740.
"Acquisition and Analysis of the Impedance Cardiogram (ICG) in the Detection of Ventricular Arrhythmias," Dempsey et al, Proc. 16th Annual Int. Conf. of IEEE Engineering in Medicine and Biology Society (1994), pp. 886-887.

* cited by examiner

*Primary Examiner* — Tammie K Heller

(57) ABSTRACT

In a method and implantable medical device for ventricular tachyarrhythmia detection and classification, upon detection of a ventricular tachyarrhythmia based on an electrocardiogram signal, cardiogenic impedance data representative of ventricular volume dynamics are collected and used for classifying the detected tachyarrhythmia as stable or unstable. In the latter case but typically not in the former case, defibrillation shocks or other forms of therapy are applied to combat the unstable ventricular tachyarrhythmia.

29 Claims, 7 Drawing Sheets

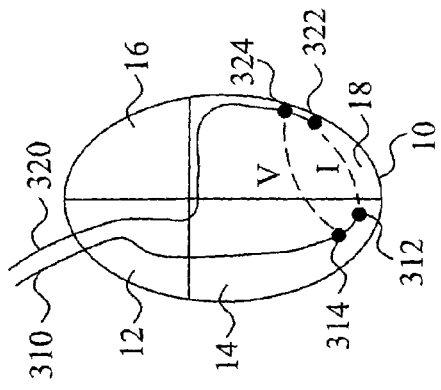
Fig. 5A
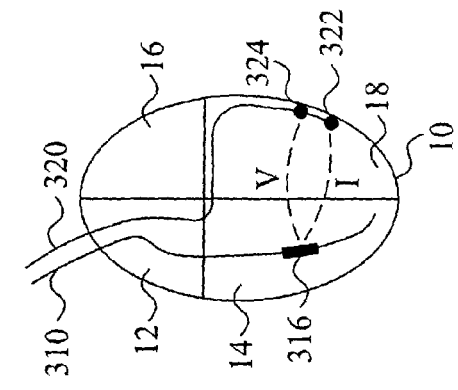
Fig. 5B
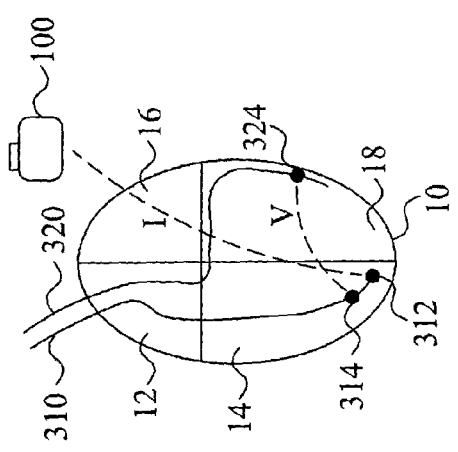
Fig. 5C
Fig. 5D
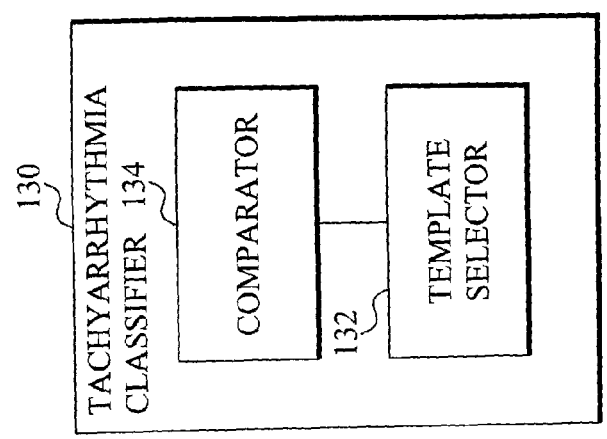
Fig. 4

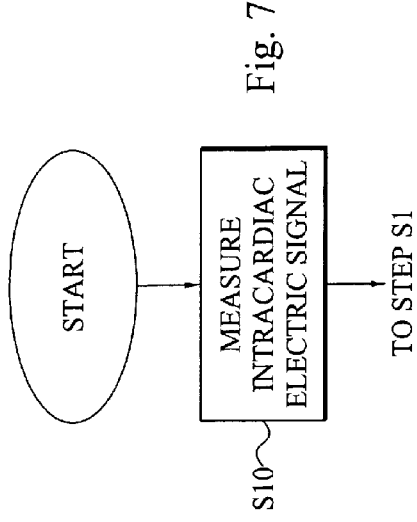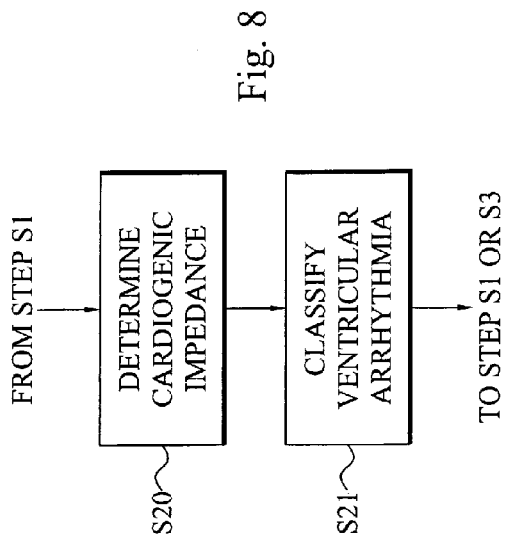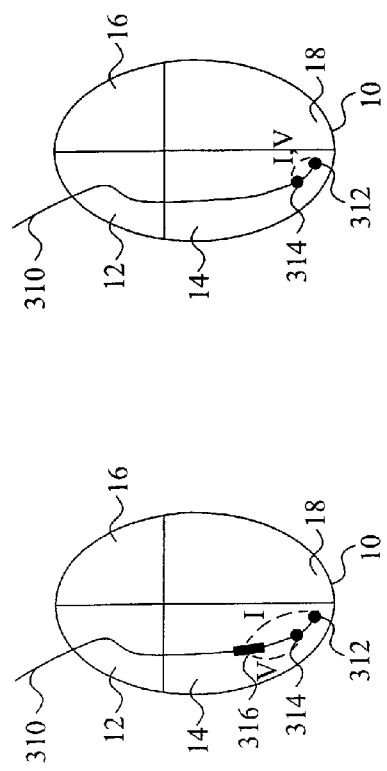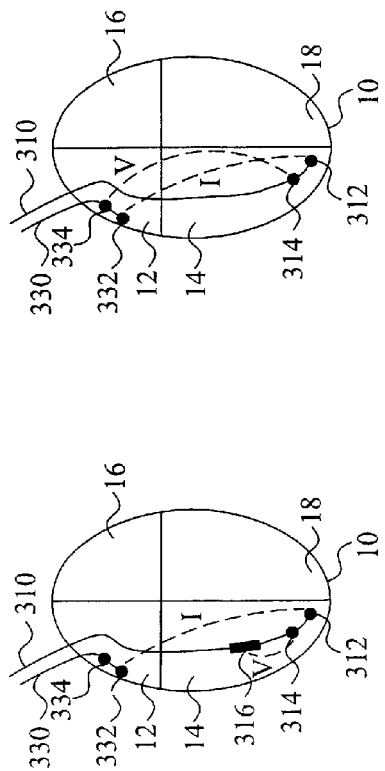

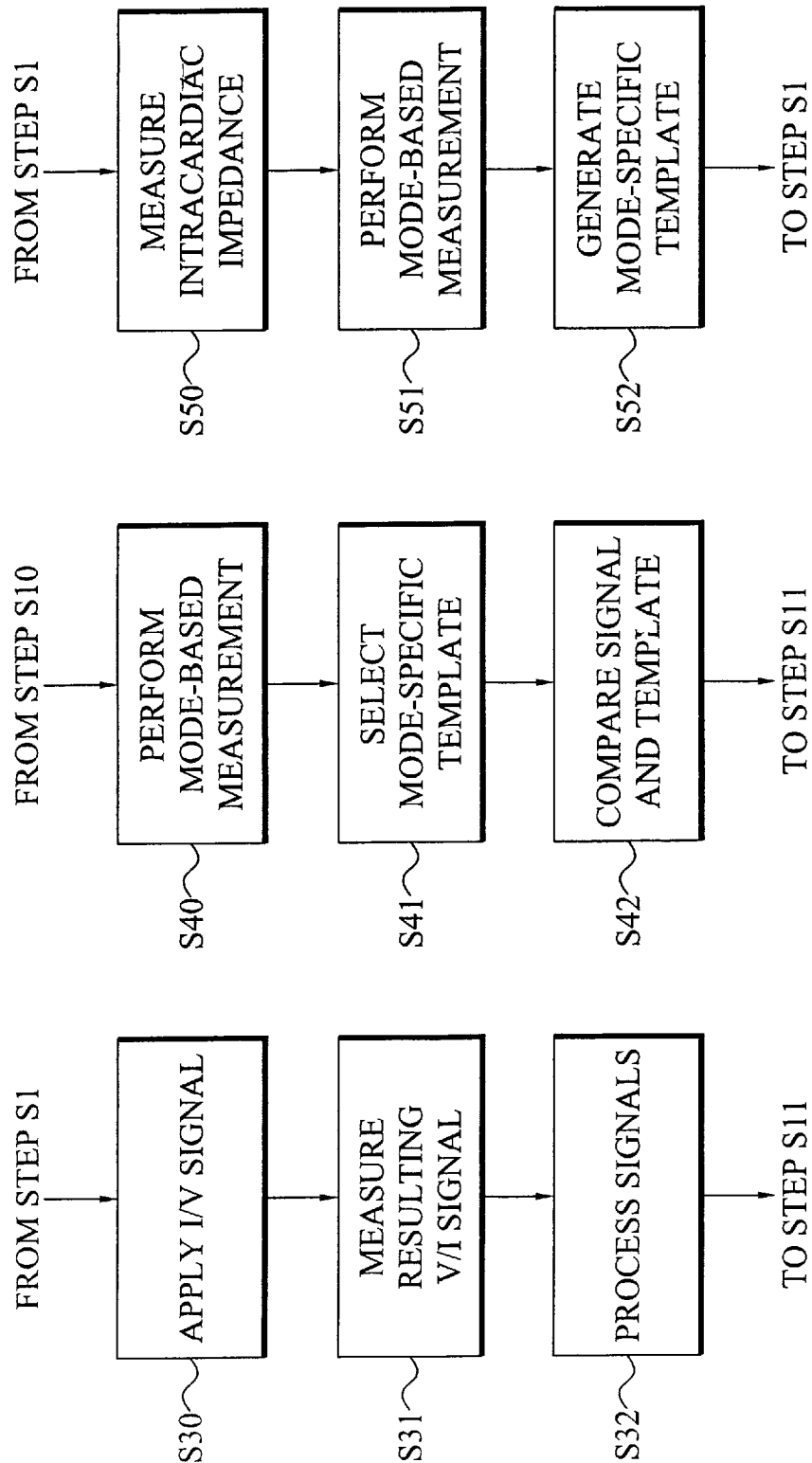

IMPLANTABLE MEDICAL DEVICE AND A METHOD COMPRISING MEANS FOR DETECTING AND CLASSIFYING VENTRICULAR TACHYARRHYTHMIAS

BACKGROUND OF THE INVENTION

1. Field of the Invention

The present invention generally relates to heart conditioning, and in particular to ventricular tachyarrhythmia detection allowing a discrimination between stable and unstable tachyarrhythmia.

2. Description of the Prior Art

Implantable medical devices (IMDs), including implantable cardiac defibrillators and pacemakers, can today be used for detecting and combating ventricular tachyarrhythmia in IMD patients. Ventricular tachyarrhythmias, for example ventricular fibrillation or tachycardia, need to be detected as early as possible as they may otherwise lead to the death of the patient if not quickly terminated. As a consequence, once tachyarrhythmia is detected, the IMD will combat it by delivering one or more defibrillation or cardioversion shocks.

Such defibrillation shocks are very uncomfortable to the patient and the risks of inappropriate and unnecessary shock applications should therefore be minimized.

Today different techniques can be used for detecting a ventricular fibrillation. A typical example is to measure the intervals between ventricular depolarization, i.e. ventricular cycle length (VCL). However with the techniques employed today, tachyarrhythmia may be detected and shocks may be applied even though the tachyarrhythmia is stable, temporary and would pass off by itself. Thus, detection techniques of today are not able to discriminate between unstable tachyarrhythmias that indeed should be combated by defibrillation shocks and other stable tachyarrhythmias that do not need any shock therapy.

U.S. Pat. No. 5,311,874 discloses a method for tachycardia discrimination. In a first embodiment, a cardiac biopotential signal is recorded and processed to identify a number of feature values representing maximum and minimum values of a complex in the signal, corresponding to a complete cardiac cycle. Firstly, the complex is classified as a baseline complex or a non-baseline complex based on the cycle length of the complex. If the complex is classified as a non-baseline complex, an extensive and very complex processing of its feature values is conducted to subsequently arrive at a discrimination point in a plane defined by a similarity vector and a dissimilarity vector. Depending on where this point is in the plane, the non-baseline complex is classified as a ventricular tachycardia (VT) or non-VT complex. In a second embodiment, a corresponding complex signal processing is performed but for discriminating between hemodynamically stable and unstable ventricular tachycardias. In this case, the input signal can be a signal or condition related to the hemodynamics of the heart, such as pressure, flow or impedance.

United States Published Patent Application No. 2005/0154421 discloses a technique for reducing inappropriate delivery of therapy to treat ventricular tachyarrhythmias caused by supraventricular tachycardia (SVT). The document specifies that SVT can be conducted to the ventricles and lead to short VCLs that would imply ventricular tachyarrhythmia. Their technique is based on measuring multiple VCLs over a defined time period. The number of such cycles that have a length shorter than a given threshold is determined and used as a basis for detecting ventricular tachyarrhythmia. If tachyarrhythmia is detected, it is determined whether the tachyarrhythmia is due to SVT or may indeed be lethal. This determination can be based on measured VCLs and atrial cycle lengths (ACLs), measured activity level of the patient or intracardiac pressure measurements.

If it is determined that the tachyarrhythmia is due to SVT no therapy or a modified form of therapy is applied, while otherwise the patient will be shocked by the IMD.

However, SVTs may indeed cause unstable ventricular tachyarrhythmias that are lethal to the patient and should be treated by defibrillation shocks. Thus, the discrimination between application of shocks or no shocks based on whether the tachyarrhythmia originates from SVTs, as determined by the document US 2005/0154421, may lead to incorrect decisions whether the patient should be shocked.

Furthermore, the technique disclosed in U.S. Pat. No. 5,311,874 is marred by the disadvantage of requiring extensive signal processing that will quickly drain the power supply when implemented in an IMD and also occupy a substantive portion of the processing capacity of the IMD. Furthermore, the document uses the same signal for classifying a signal complex as baseline or non-baseline as for classifying a non-baseline complex as hemodynamically stable or unstable which is not optimally.

SUMMARY OF THE INVENTION

The present invention overcomes these and other drawbacks of the prior art arrangements.

It is a general object of the present invention to provide an implantable medical device having the capability of detecting and classifying ventricular tachyarrhythmias.

It is another object of the invention to provide a tachyarrhythmias detection that can reliably discriminate between ventricular tachyarrhythmias that should be treated with defibrillation shocks and those tachyarrhythmias where the heart will spontaneously recover back to normal operation.

Briefly, the present invention involves an implantable medical device having a tachyarrhythmia detector arranged for detecting a ventricular tachyarrhythmia in a heart of subject. The detector uses electrical signals collected by the IMD for detecting conditions indicative of the presence of a tachyarrhythmia. These electrical signals correspond to electrocardiogram or intracardiac electrocardiogram. Based on such a tachyarrhythmia detection, an impedance determining unit generates a cardiogenic impedance signal representative of the volumetric dynamics of the at least one of the ventricles in the subject's heart. The impedance signal is preferably an average signal measured over several heart beats. A tachyarrhythmia classifier of the IMD uses the generated cardiogenic impedance signal for classifying the tachyarrhythmia as stable (no or only marginal blood pressure drop) or unstable (significant reduction in blood pressure). In the latter case, the medical device applies an appropriate therapy to combat the unstable tachyarrhythmia, such as a defibrillation shock. In the former case, the stable tachyarrhythmia may spontaneously cease and normal heart operation is restored without the need for defibrillation shocks.

The present invention preferably uses special impedance vectors that are particularly adapted for capturing the ventricular volume dynamics. Such vectors in particular include quadropolar impedance measurements between the left and right ventricles or between the right atrium and ventricle.

The tachyarrhythmia classification is preferably performed using signal morphology comparisons of the generated cardiogenic impedance signal and pre-defined signal templates. Most preferably, different such signal templates are available and representative of the cardiogenic impedance at different body states that affect the impedance signal, such as body posture, heart rate and body activity. In connection with tachyarrhythmia detection, a current body state (posture, heart rate and/or activity) is also determined. This state data is then employed for selecting a correct impedance template to use in the morphological signal comparison.

The present invention also relates to a heart conditioning method, preferably implemented in an implantable medical device.

The invention offers the following advantages:
- Allows discrimination between ventricular tachyarrhythmias that should be treated with electrical shocks or pacing and tachyarrhythmias for which no treatment is needed;
- Does not need the use of extra sensor equipment but can use electrodes of traditional cardiac leads;
- Uses a first signal representing a first heart related quantity for tachyarrhythmia detection and second different signal representing a second heart related quantity for tachyarrhythmia classification;
- Increases the specificity of tachyarrhythmia detection tremendously; and
- Can be used to monitor the progression of the tachyarrhythmia.

Other advantages offered by the present invention will be appreciated upon reading of the below description of the embodiments of the invention.

BRIEF DESCRIPTION OF THE DRAWINGS

FIG. 4 is a schematic block diagram of a tachyarrhythmia classifier according to an embodiment of the present invention.

FIGS. 5A to 5H are schematic diagrams of preferred intracardiac lead positions and impedance vectors useful according to the present invention.

FIG. 7 is a flow diagram of an additional step of the heart conditioning method.

FIG. 8 is a flow diagram illustrating the step of detecting unstable ventricular tachyarrhythmia of FIG. 6 in more detail according to an embodiment of the present invention.

FIG. 9 is a flow diagram illustrating the step of determining cardiogenic impedance of FIG. 8 in more detail according to an embodiment of the present invention.

FIG. 10 is a flow diagram of additional steps of the heart conditioning method.

FIG. 11 is flow diagram of additional steps of the heart conditioning method.

DESCRIPTION OF THE PREFERRED EMBODIMENTS

Figure 3:
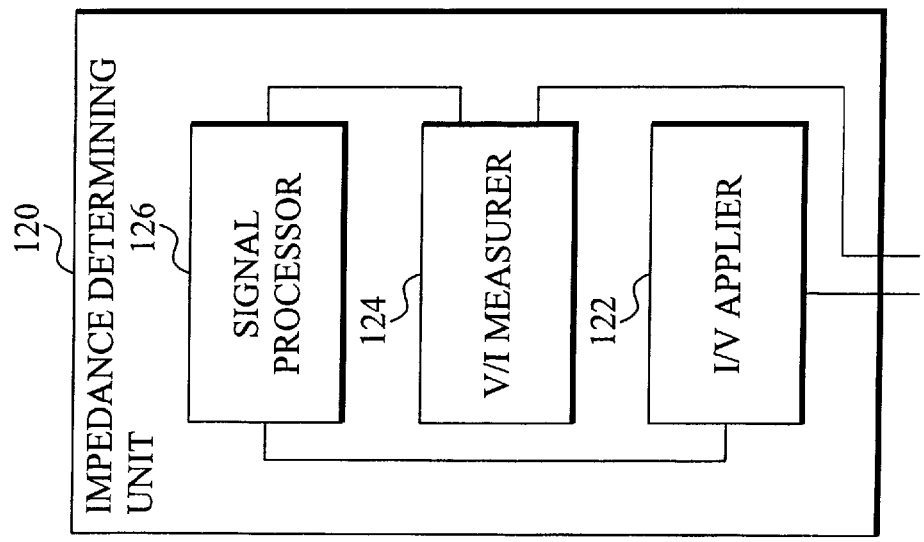
FIG. 3 is a schematic block diagram of an impedance measuring unit according to an embodiment of the present invention.

The present invention generally relates to implantable medical devices and methods for detecting and classifying different forms of ventricular tachyarrhythmia.

As is known in the art, ventricular tachyarrhythmia relates to medical conditions in which the electrical activity of the heart is irregular and/or faster than normal and where the abnormal activity originates from or is caused by the left and/or right ventricle. Ventricular tachyarrhythmias are traditionally defined as ventricular tachycardia, ventricular flutter and ventricular fibrillation.

Ventricular tachycardia is a potentially life threatening cardiac tachyarrhythmia originating in the ventricles. The tachycardia is characterized by increased heart rate, often in the interval of 120 to 250 beats per minutes. It may degrade into the more serious ventricular fibrillation.

Ventricular flutter is a ventricular tachyarrhythmia characterized electrocardiographically by smooth undulating waves with QRS complexes merged with T waves, and a rate of approximately 250 beats per minute. If untreated it usually progresses to ventricular fibrillation.

Ventricular fibrillation is a condition with uncoordinated contraction of the cardiac muscle of the ventricles in the heart. As a result, the heart fails to adequately pump the blood and hypoxia may occur. If continuing for more than a few seconds, blood circulation and blood pressure will drop significantly.

According to the present invention, it has been realized that not all forms for ventricular tachycardias/tachyarrhythmias are life-threatening and should be treated by defibrillation shocks. In clear contrast, a ventricular tachycardia could be characterized by a stable heart rhythm that as a matter of course gradually will return to normal heart rates even without any applied treatment. Such stable forms of ventricular tachycardia can occur because of heavy exercise and or stress of the patient. As defibrillation shocks are tremendously uncomfortable to the patient and may even have severe consequences, such shocks should ideally not be applied to ventricular tachyarrhythmias that spontaneously will revert to normal heart operation.

These stable forms of ventricular tachyarrhythmias are characterized by stable blood pressure or only temporarily and slightly decreasing (typically less than 20%, preferably less than 10%, such as less than 5% or less than 1%) blood pressure. However, lethal and unstable forms of ventricular tachyarrhythmias, in clear contrast, lead to large drops in blood pressure, typically with about or even more than 50%. In severe conditions, the blood pressure could even fall as low as 50 mmHg for the systolic pressure.

Therefore, in order to be able to provide efficient and correct treatment to tachyarrhythmia patients it is important to discriminate between stable tachyarrhythmia with stable heart rhythm and blood pressure and unstable tachyarrhythmia with large reductions in blood pressure.

United States Published Patent Application No. 2005/0154421 described in the background section basically makes a discrimination between, what is denoted, lethal arrhythmias and supraventricular tachycardia (SVT) and similar forms of so-called non-lethal arrhythmias. However, that is not a satisfactory discrimination as SVT may indeed be unstable and of considerable danger to a patient if left untreated. As a consequence, the techniques employed in that prior art document may miss unstable tachyarrhythmias, causing severe patient problems or even deaths.

In clear contrast to the prior art, the present invention has discovered that it is possible to use cardiogenic impedance signals representative of volumetric dynamics of the heart ventricles for, in a reliable and efficient way, classify detected ventricular tachyarrhythmias as stable or unstable tachyarrhythmias as defined herein. This cardiogenic impedance based arrhythmia classification is used together with an electrocardiogram-based tachyarrhythmia detection. Thus, the present invention uses two fundamentally different signals representative of the operation of the heart in the detection and classification. The detection uses electrocardiogram signal that are much better than impedance signals for, in an efficient and simple way, detecting a tentative tachyarrhythmia. However, these electrocardiogram signals are not well-suited for tachyarrhythmia classification, in which the cardiogenic impedance of the present invention is a much better candidate. Therefore by employing these two fundamentally different signal types, the detection and classification of the present invention will be more correct and reliable as compared to the prior art techniques that use one and the same signal for both tachyarrhythmia detection and classification.

Figure 1:
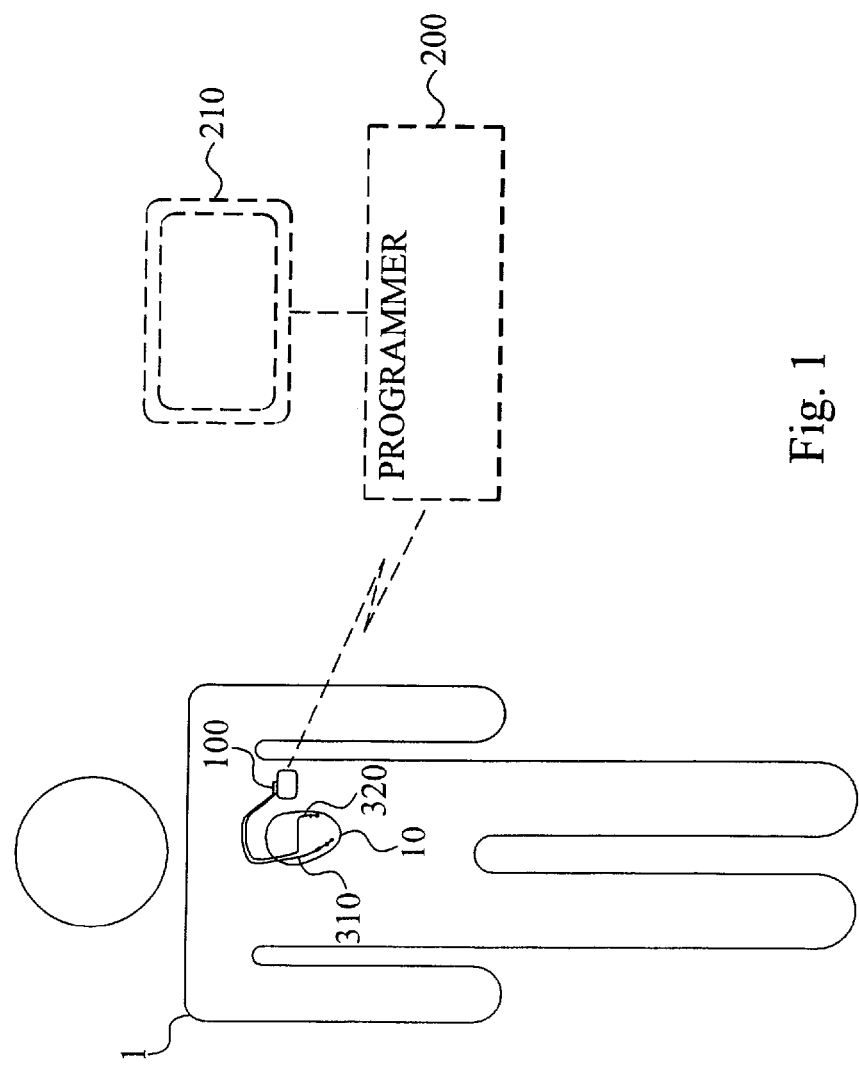
FIG. 1 is a schematic overview of a subject having an implantable medical device according to the present invention.

FIG. 1 is a schematic overview of a patient 1 having an implantable medical device, IMD, 100 according to the present invention. In the figure, the IMD 100 is illustrated as a device that monitors and/or provides therapy to the heart 10 of the patient 1, such as a pacemaker, cardiac defibrillator or cardioverter. The IMD 100 is, in operation, connected to one or more, two in the figure, intracardiac leads 310, 320 inserted into different heart chambers, the right and left ventricles in the figure.

The figure also illustrates an external programmer or clinician's workstation 200 that can communicate with the IMD 100. As is well known in the art, such a programmer 200 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the programmer 200 before display to a clinician on a connected display screen 210. In the light of the present invention, such diagnostic data can include cardiogenic impedance data measured by the IMD 100 and/or other diagnostic data relating to ventricular tachyarrhythmia detection and classification.

Figure 2:
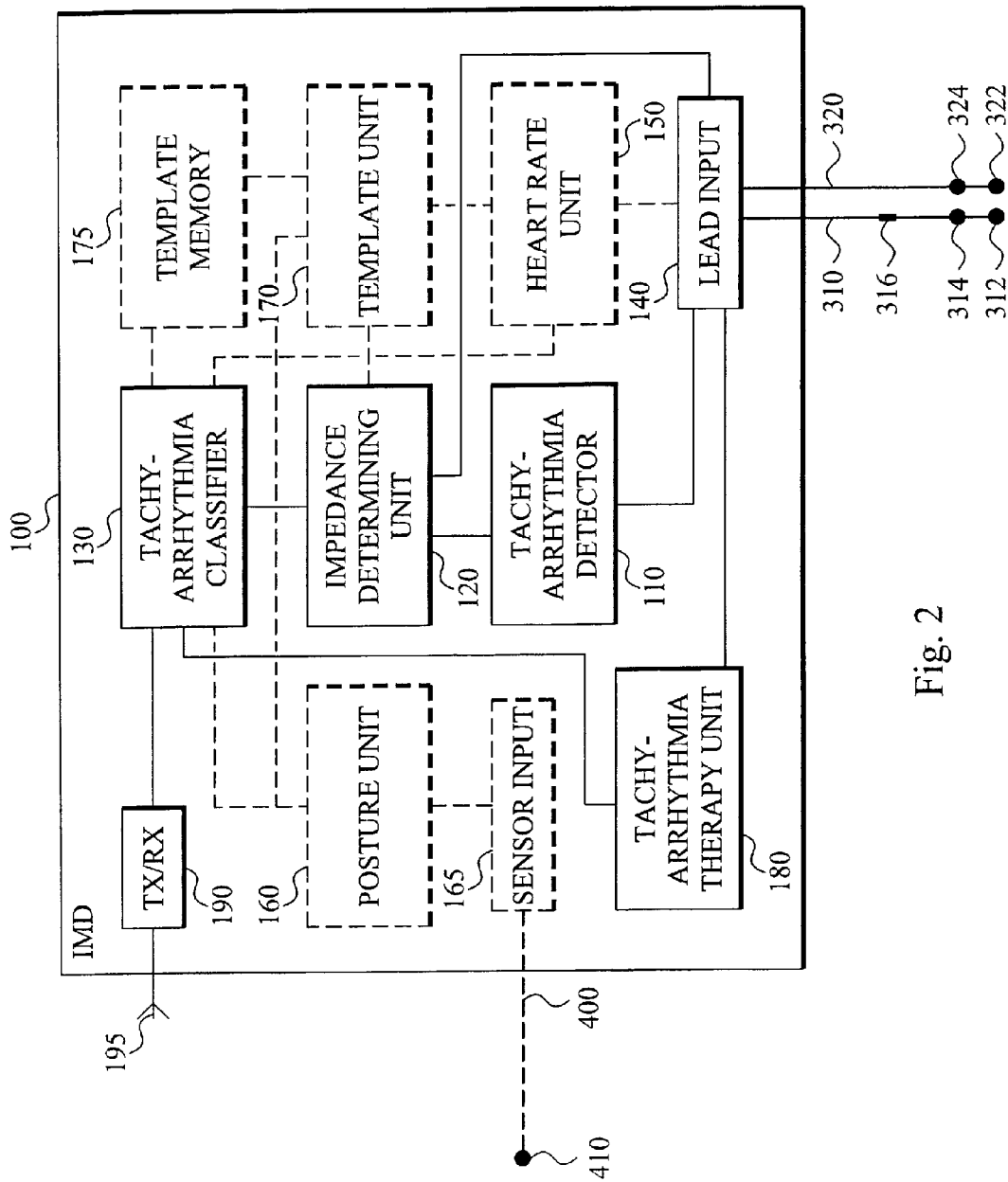
FIG. 2 is a schematic block diagram of an implantable medical device according to an embodiment of the present invention.

FIG. 2 is a schematic block diagram of an IMD 100 according to the present invention. The IMD 100 comprises a tachyarrhythmia detector 110 arranged for detecting the presence of a ventricular tachyarrhythmia in a heart of a subject. This tachyarrhythmia detector 110 is preferably connected to a lead input 140 of the IMD 100. The lead input 140 is in turn connectable to one or more cardiac leads 310, 320, preferably intracardiac leads 310, 320. These leads each comprises one or more electrodes 312, 314, 316; 322, 324 for measuring different electrical parameters in the subject's heart and/or applying electrical pulses or shocks to the heart. In this context different forms of lead electrodes well-known in the art can be used, including lead tip electrodes 312, 322, lead ring electrodes 314, 324 and lead coil electrodes 316. The electrodes 312, 314, 316; 322, 324 preferably measure intracardiac electrical signals that are forwarded through the leads 310, 320 and lead input 140 to the tachyarrhythmia detector 110 for processing. The detector 110 then uses these intracardiac electric signals for detecting the presence of a ventricular tachyarrhythmia. These electric signals preferably represent electrocardiogram (ECG) signals and preferably an intracardiac electrocardiogram (IEGM) signals.

For example, the collected and processed intracardiac electrocardiogram signals could represent or be representative of the ventricular beating rate. In such a case, the detector 110 can signal a tentative ventricular tachyarrhythmia if the sensed ventricular rate exceeds a pre-defined threshold value. The detection can preferably be at least partly time-based if, for example, the detector 110 collects ventricular rate data over a time interval and determines an average value. This average value can then be compared to the threshold value. In an alternative approach, the detector 110 compares multiple collected ventricular rate values with the threshold and signals a tentative ventricular tachyarrhythmia if at least a minimum selected portion of the rate values exceed the threshold value.

In an alternative or complementary embodiment, the tachyarrhythmia detector processes electrocardiogram signals for detecting the presence of premature ventricular contractions (PVCs, also known as ventricular premature beats or extrasystole in the art). PVCs are characterized by starting of depolarization in the ventricle instead of the sinus node. This causes a form of irregular heart beat in which the ventricle contracts prematurely. The detector 110 can then signal a ventricular tachyarrhythmia if such a PVC is detected. Alternatively, tachyarrhythmia is signaled if at least a minimum number of PVCs are detected by the detector 110 within a defined time interval.

The collected electrical cardiac signals can also or alternatively be processed by the tachyarrhythmia detector 110 for detecting any irregular atrioventricular synchrony. Thus, any irregularity in the physiological condition of atrial electrical activity followed by ventricular electrical activity with the interval between being that necessary for impulse conduction from atria to ventricles can be used for detecting the presence of ventricular tachyarrhythmia by the detector 110.

The IMD 100 also has an impedance determining unit 120 connected to the tachyarrhythmia detector 110 and the lead input 140. This determining unit 120 is arranged for determining, based on electrical signals, a cardiogenic impedance signal, preferably a complex impedance signal, representative of volumetric dynamics of the right and/or left ventricle. This cardiogenic impedance signal, thus, closely follows the blood filling and emptying dynamics of at least one heart ventricle, in particular the ventricle blood filling dynamics.

In a preferred embodiment, the impedance determining unit 120 is responsive to a tachyarrhythmia detection signal from the tachyarrhythmia detector 110. Thus, the determining unit 120 preferably collects and processes electrical signals in response to reception of such a detection signal to generate the cardiogenic impedance signal.

The determining unit 120 preferably measures the cardiogenic impedance during multiple time periods of different heart beats. For example, the determining unit could determine impedance values for several successive heart beats or for several timely separated heart beats occurring in a defined time interval. These different cardiogenic impedance values over different heart beats can then be collectively processed by the determining unit 120 to form an average cardiogenic impedance signal. It is also possible to use a floating average value calculation so that the determined cardiogenic impedance signal is an average of the cardiogenic impedance values collected during the last N measured heart intervals, where N is a predefined integer equal to or larger than two, preferably 3-20. Thus usage of such a (floating) average reduces the variability in impedance signal that can occur during tachyarrhythmia situations. As a consequence, a more reliable tachyarrhythmia classification is possible by using an average cardiogenic impedance signal.

The determined cardiogenic impedance signal can be a complex cardiogenic impedance signal, i.e. comprising both a real and imaginary part. These respective parts can then be separately or collectively processed in the tachyarrhythmia classification of the present invention. For example, the real and imaginary parts can be employed for calculating a phase angle between them. In a preferred implementation, the average of the two impedance components during a period of time, such as 5 to 30 seconds, is used. Such average signals reduce the influence of, for instance, the respiratory components of the cardiogenic impedance signal. During unstable ventricular arrhythmia, the complex cardiogenic impedance signal becomes comparatively more resistive so that the impedance vector will be moved towards the real axis in a graph having a real axis and an imaginary axis. Thus, a calculated phase angle of the complex cardiogenic impedance can be an efficient way of discriminating between stable and unstable tachyarrhythmia. For example, if the phase angle is within a first angle interval the arrhythmia is classified as unstable whereas in another angle interval it is regarded as stable. Correspondingly, the relationship between the real part and the imaginary part of the impedance vector can be used in the discrimination.

FIG. 3 is a schematic block diagram illustrating a possible implementation of the impedance determining unit 120 of FIG. 2. The determining unit 120 comprises a signal applier 122 for applying, over two electrodes of the lead(s) connectable to lead input of the IMD, an electrical signal to at least a portion of the heart. This signal applier 122 is preferably responsive to the detection signal from the tachyarrhythmia detector. As a consequence, the applier 122 applies the signal to the heart portion lying between the selected lead electrodes based on reception of this detection signal.

The signal applier 122 can be arranged for generating and applying a predefined current or voltage signal. As is known in the art, such an applied current or voltage signal, preferably current signal can be a stepwise or gradually changing (current) signal.

A signal measurer 124 is implemented in the determining unit 120 for measuring, using at least two electrodes of the lead(s) connectable to the lead input of the IMD, a resulting electrical signal over at least a portion of the heart. This measurer 124 preferably measures a resulting voltage signal, if the signal applier 122 applied a current signal or pulse, and measures a resulting current signal, if the applier 122 applied a voltage signal.

The impedance determining unit also comprises a signal processor 126 for determining a cardiogenic impedance signal based on the electrical signal applied by the signal applier 122 and the resulting electrical signal measured by the signal measurer 124. The signal processor 126 employs well known signal processing techniques for determining the cardiogenic part of the impedance signal based on the raw input electrical signals. Briefly, the input measured AC voltage is optionally pre-amplified and an integrated by calculating the voltage area of the signal per pulse. The applied AC current signal is also integrated by calculating the current area of the signal per pulse. The integrated absolute impedance can then be calculated in block as the quotient between the voltage area and the current area. This raw impedance signal may be further processed in a filter chain including, for example, a high-pass filter followed by a low-pass filter. The filter output is A/D converted to form the desired output cardiogenic impedance signal $Z_c$.

The units 122 to 126 of the impedance determining unit 120 may be provided as hardware, software or a combination of hardware and software. A distributed implementation is also possible where at least one of the units 122 to 126 is implemented elsewhere in the IMD.

The present invention preferably also uses selected impedance measurement vectors that are better used for catching and representing the volume dynamics of the ventricles. Is has been discovered that the measurement electrode configurations, i.e. impedance vectors, have an important role for the information in the impedance signal. The information in the signal consists mainly of two parts, the impedance variation near the electrodes and the impedance in the tissue between the electrodes. The near electrode impedance including the double layer impedance is not representative of the volumetric ventricle dynamics but is dominating in most bipolar configurations. As is known in the art, in a bipolar measurement the excitation current (voltage) signal is applied to the same two electrodes as used for detecting the resulting voltage (current) signal.

There are three main techniques to reduce this near impedance and favor the relevant tissue impedance. Firstly, large electrode areas could be used in combination with a bipolar measurement. Such large electrodes are normally the IMD can or case and defibrillation coils. Secondly, a tripolar measurement where a large area electrode (coil or can/case) is a common electrode for the current excitation and voltage detection can be used. The other two electrodes do not have any surface area restrictions. Thirdly, a quadropolar measurement vector can be used without any limitations to the electrode size and still the undesired impedance contribution originating from the electrodes near field is reduced.

FIGS. 5A to 5D are schematic illustrations of different impedance measuring vector constellations that are particularly suitable for following volume variations in the left ventricle, while FIGS. 5E to 5H illustrate corresponding impedance vectors for following volume dynamics of the right ventricle. In these figures, the reference number 12 denotes the right atrium, reference number 14 the right ventricle, reference number 16 the left atrium and reference number 18 the left ventricle of a heart 10. In the respective figures, only those electrodes of the leads employed for signal application and measurement are illustrated. It is though anticipated by the present invention that the leads may include other electrodes and sensors in addition to the illustrated ones.

In FIG. 5A a first intracardiac lead 310 equipped with a tip electrode 312 and a coil electrode 316 is inserted into the right ventricle 14. A corresponding lead 320 with a tip electrode 322 and ring electrode 324 is placed in the left ventricle. A preferred quadropolar measurement is then obtained by, for example, applying a current pulse between the right 312 and left 322 tip electrodes and measuring a resulting voltage signal between the right coil 316 and left ring 324 electrodes. FIG. 5B is a slightly different arrangement, where a ring electrode 324 of the right intracardiac lead replaces the coil electrode as one of the voltage sensing electrodes.

An alternative when using unipolar left ventricular leads 320 is to replace the left ventricular ring electrode with the case 100 on a left pectoral position. FIG. 5C illustrates this arrangement. Another alternative for high voltage leads 310 is to measure tripolarly between the right ventricular coil 316 and the left ventricular tip 322 and ring 324 electrodes as illustrated in FIG. 5D.

Volume dynamics of the right ventricle can be obtained through cardiogenic impedance measurements using a high voltage lead 310 as applying an excitation current between the right ventricular coil 316 and the right ventricular tip 312, while sensing is performed between the coil 316 and the right ventricular ring 314, which is illustrated in FIG. 5E. FIG. 5F illustrates an alternative by measuring bipolarly between right ventricular tip 312 and ring 314 electrodes. This impedance vector is though less precise and not as useful for representing volumetric dynamics of the right ventricle as the impedance vectors of FIGS. 5E, 5G and 5H. In FIGS. 5G and 5H, the right ventricular lead 310 is complemented with a right atrial lead 330. In such a case, voltage detection can be made between the right ventricular coil 316 and right ventricular ring 314, while the excitation current is applied between the right ventricular tip electrode 312 and the right atrial tip 332 or right atrial ring 334 electrodes, see FIG. 5G. FIG. 5H shows another quadropolar measurement where two low voltage leads 310, 330 are used. In such a case, the current excitation is applied between one of the right ventricle ring 314 and tip 312 electrodes and one of the right atrial ring 334 and tip 332 electrodes and the resulting voltage is measured between the other of the right ventricle ring 314 and tip 312 electrodes and the other of the right atrial ring 334 and tip 332 electrodes.

Returning to FIG. 2, the IMD 100 also comprises a tachyarrhythmia classifier 130 connected to the impedance measuring unit 120. This classifier 130 receives the ventricle volumetric dynamics representing cardiogenic impedance signal from the determining unit 120 and uses it for classifying the ventricular tachyarrhythmia detected by the detector 110 as stable or unstable based on the impedance signal. The cardiogenic impedance signal representative of the ventricle volumetric dynamics shows a decrease in peak-to-peak values during unstable but not stable ventricular tachyarrhythmia. Thus, the tachyarrhythmia classifier 130 can monitor such peak-to-peak values over a time interval to detect any decrease and thereby classify the tachyarrhythmia as unstable.

Figure 12:
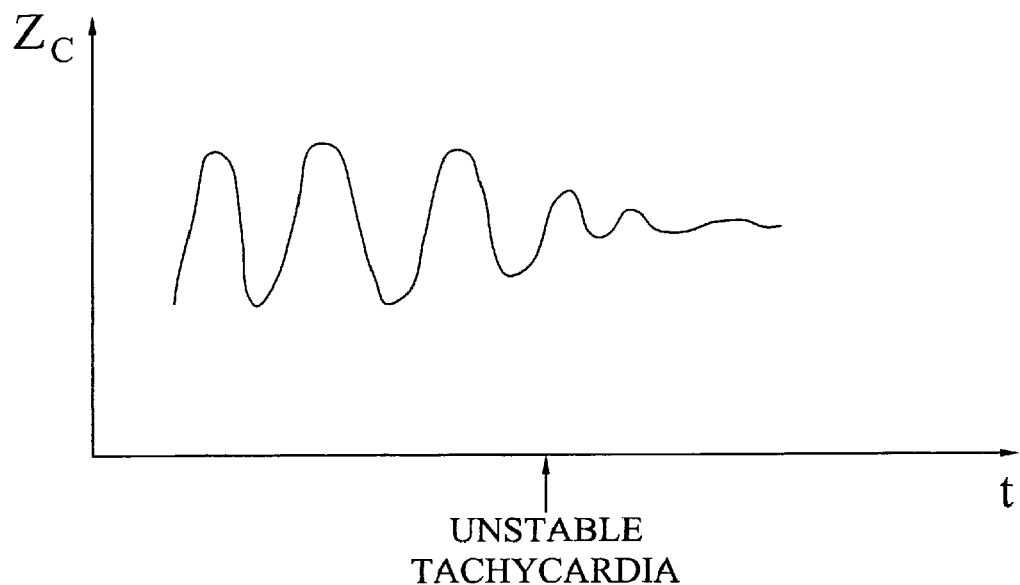
FIG. 12 is a diagram illustrating cardiogenic impedance at the onset of unstable tachycardia.

FIG. 12 is a diagram illustrating a measured cardiogenic impedance signal according to the present invention. It is clear from the figure at the onset of the unstable tachyarrhythmia, in this case unstable tachycardia, the peak-to-peak values are reduces significantly and might even be almost non-existing. The classifier can then base the tachyarrhythmia classification of such a peak-to-peak reduction exceeds a predefined threshold value.

In a more elaborated embodiment, the IMD 100 also comprises a template unit 170 connected to the impedance determining unit 120. The template unit 170 receives cardiogenic impedance data collected by the determining unit 120 during normal heart function, i.e. no detected tachyarrhythmia, and/or during previously classified stable or unstable tachyarrhythmia periods. This received impedance data is processed by the template unit 170 for the purpose of determining one or more signal templates that are stored in a connected template memory 175. The templates can then be used by the tachyarrhythmia classifier 130 together with cardiogenic impedance data from the determining unit 120 to classify a detected tachyarrhythmia as stable or unstable.

The template signal is preferably determined as an average impedance template signal through averaging impedance data collected over multiple heart beats. The template will then be a waveform over the average impedance changes during a heart beat.

It is anticipated by the present invention that a same impedance vector is preferably employed for generating the impedance templates as for determining the cardiogenic impedance signal.

The template unit 170 preferably regularly updates the impedance templates in the template memory 175 over time to reflect impedance changes caused by other factors than tachyarrhythmia, such as changes to the local heart tissue environment or changes to the lead 310, 320 or lead electrodes 312, 314, 316; 322, 324 employed for collecting the raw electric signals. This means that impedance templates could for example be updated daily, weekly, monthly or even more seldom.

In a preferred implementation, the template unit 170 determines a set of multiple different standard impedance templates. The respective impedance templates can then be adapted to different patient states or conditions, which affect the impedance signals, including body position and body activity. In the latter case, the IMD 100 preferably comprises a heart rate unit 150 connected to the lead input 140, the template unit 170 and the tachyarrhythmia classifier 130. This heart rate unit 150 receives electrical signals collected by sensors or electrodes 312, 314, 316; 322, 324 of the electrical leads connectable to the lead input 140. The rate unit 150 processes the input signal for estimating a current heart rate of the patient. This heart rate is used as a representation of a current body activity. Instead of being connected to the lead input 140, the heart rate unit 150 could be connected to the impedance measuring unit 120 and receive impedance data therefrom. Such impedance data can be used for estimating a current heart rate. It is anticipated by the present invention that the heart rate unit 150 can be replaced by or complemented with other units for determining parameters representative of body activity, including accelerometers and respiratory rate determining units (could use thoracic impedance data).

In either case, impedance data is collected by the impedance measuring unit 120 as the heart rate unit 150 determines the current heart rate. The template unit 170 then uses the collected impedance data and the heart rate 150 for generating different impedance templates, where each such template is representative of the normal cardiogenic impedance at a given heart rate interval. The template memory 175 will then contain a set of different such impedance templates with different associated heart rate intervals.

Correspondingly, the IMD 100 can have a posture unit 160 connector to a sensor input 165 in turn connectable to a lead or catheter 400 equipped with a posture sensor 410. This sensor 410 could be attached to a dedicated posture lead 400, be positioned directly onto or inside the IMD 100 or be attached to one of the intracardiac electrical leads 310, 320. The posture unit 160 is further connected to the template unit 170 and the tachyarrhythmia classifier 130. In similarity to the heart rate unit 150, the posture can determine different current body postures, such as standing, lying (on the back, on the stomach (in prone position), on the left side or on the right side) or sitting, in connection with collecting impedance data. In such a case, different impedance templates can be generated by the template unit 170 for different body postures and stored in the memory.

The two embodiments described above can of course be combined. In such a case, an impedance template can be associated with both a body posture and a heart rate interval.

FIG. 4 is a schematic block diagram of an embodiment of the tachyarrhythmia classifier 130 of FIG. 2 adapted for usage in connection with different pre-defined impedance templates. The classifier 130 comprises a template selector 132 that receives input data from the heart rate unit and/or body posture unit. The selector 132 fetches a correct impedance template from the template memory based on the rate and/or posture data to obtain a most appropriate template that is adapted to the current patient posture and activity level.

A comparator 134 of the classifier 130 receives the impedance template from the template selector and the impedance data generated by the impedance determining unit. The comparator 134 compares the data to the template to classify the tachyarrhythmia as stable or unstable. In a preferred implementation, the comparator performs a morphological comparison of the impedance signal and the signal template. This morphological comparison can be performed by determining a parameter representative of a difference between the template and the impedance signal, preferably a mean square error. If this (error) parameter exceeds a predefined threshold, the tachyarrhythmia is classified as unstable if the template represents an impedance signal during normal heart operation or stable ventricular tachyarrhythmia. Correspondingly, the tachyarrhythmia is classified as stable if the template instead represents an impedance signal collected during a previous period of unstable ventricular tachyarrhythmia. It is anticipated by the present invention that multiple threshold values could be employed instead. For example, if the discrimination parameter is within a first value interval, the tachyarrhythmia could be classified as stable, if it is within a second interval, the tachyarrhythmia could be tentative unstable and more measurements should be collected, while within a third interval the tachyarrhythmia is clearly unstable.

The units 132 and 134 of the tachyarrhythmia classifier 130 may be provided as hardware, software or a combination of hardware and software. A distributed implementation is also possible where at least one of the units 132 and 134 is implemented elsewhere in the IMD.

The usage of multiple predefined impedance templates adapted to different patient body states and morphological signal comparisons markedly improves the reliability in classifying the ventricular tachyarrhythmias. This means that the risk of incorrectly applying tachyarrhythmia therapies, such as defibrillation shocks and/or anti-tachycardi pacing pulses, for stable tachyarrhythmias or, more seriously, misclassifying unstable tachyarrhythmias as stable ones will be significantly reduced.

Figure 13:
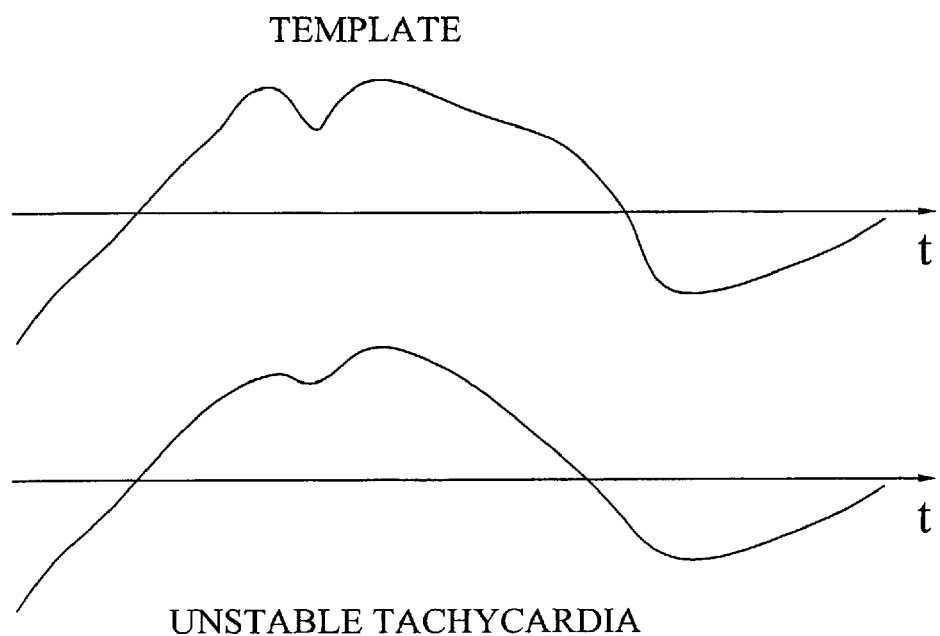
FIG. 13 illustrates the morphological difference in cardiogenic impedance between normal heart operation and unstable tachycardia.

FIG. 13 is a diagram schematically illustrating a cardiogenic impedance template during stable tachyarrhythmia at the top and a corresponding averaged cardiogenic impedance signal collected during unstable tachycardia. As is clearly seen, the two signals exhibits significant morphological differences that can easily be detected in a morphology comparison using, for instance, a mean square error method.

Returning anew to FIG. 2, the IMD 100 also comprises a tachyarrhythmia therapy unit 180 connected to the tachyarrhythmia classifier 130 and the lead input 140. If the tachyarrhythmia classifier 130 determines that a current tachyarrhythmia detected by the tachyarrhythmia detector 110 is indeed unstable, it signals the therapy unit 180. The therapy unit 180 then applies, through the lead input 140 and the connectable intracardiac leads 310, 320, an appropriate tachyarrhythmia therapy, which is well known in the art. For example, the therapy could be in the form of a high voltage defibrillation shock using a coil electrode 316. Alternatively, anti-tachycardi pacing pulses could be applied to the heart using other lead electrodes.

The IMD 100 is typically equipped with a transmitter and receiver unit 190 having a connected antenna 195 for enabling wireless communication with external units, including a programmer or clinician's workstation. The transmitter/receiver unit 190 comprises those functionalities required for transmitting data, in particular collected diagnostic data, and receiving data, in particular operation setting updates, such as encoder/decoder, modulator/demodulator, etc. The transmitter/receiver 190 and the connected antenna 195 can operate for communicating data through radio frequency based techniques. In an alternative embodiment, an inductive transmission technique is used. The antenna 195 could then be exchanged by an inductive coil. According to the present invention, the transmitter 190 can in particular communicate diagnostic data relating to the detection and classification of ventricular tachyarrhythmias. Correspondingly, the receiver 190 can receive programming parameters relative to the tachyarrhythmia detection and classification. Examples of such parameters could include information of time intervals to use when collecting impedance data and calculating average data, threshold values for detecting presence of tachyarrhythmia and classifying the tachyarrhythmias or even pre-defined impedance templates to use in the tachyarrhythmia classification.

The units 110 to 190 of the IMD 100 may be provided as hardware, software or a combination of hardware and software.

Figure 6:
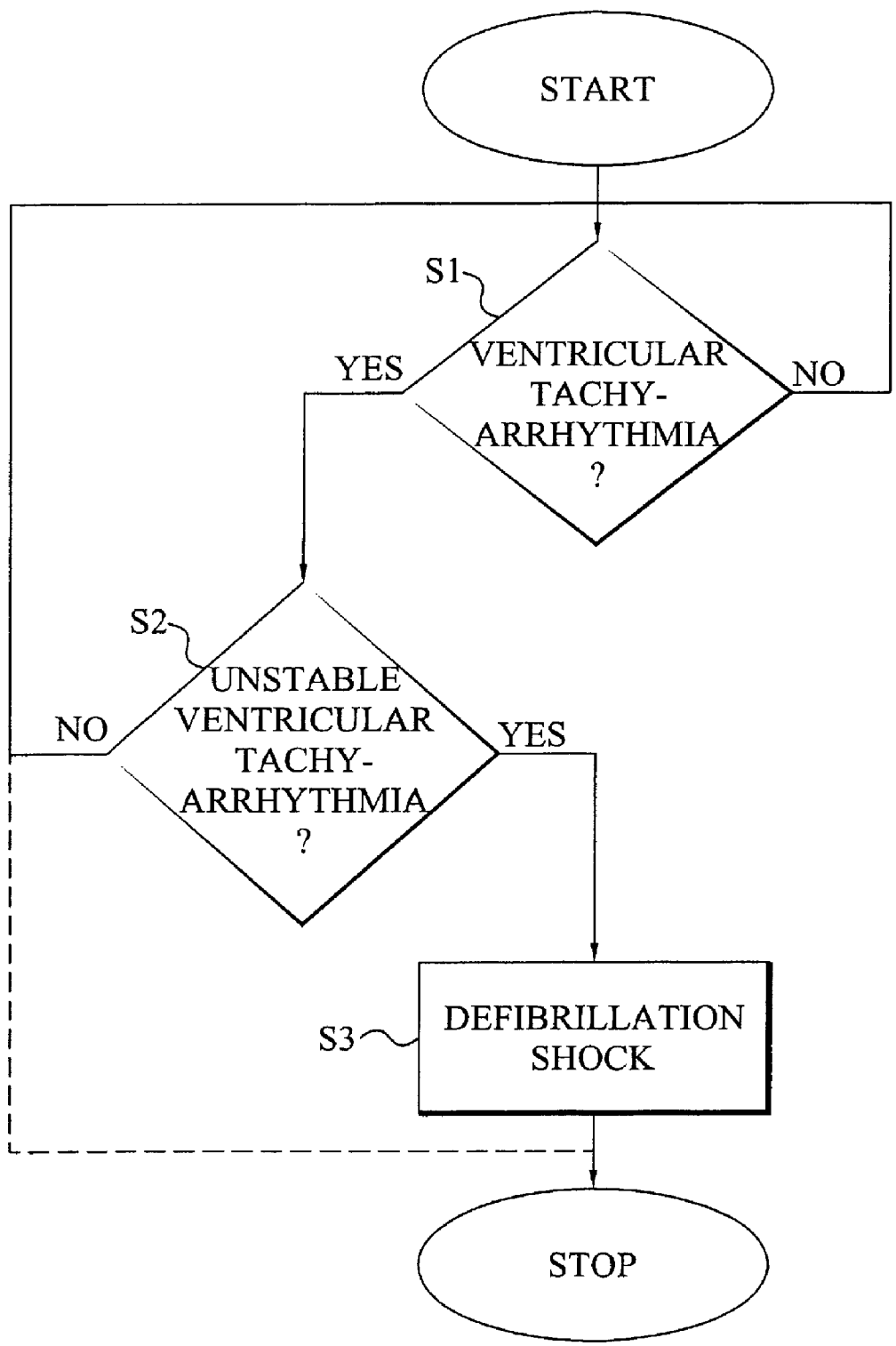
FIG. 6 is a flow diagram of a heart conditioning method according to the present invention.

FIG. 6 is a schematic flow diagram of a heart conditioning method according to the present invention. The method starts in step S1 which determines whether a ventricular tachyarrhythmia is present. This step can perform the detection continuously or, preferably, periodically at predefined at instances. If a ventricular tachyarrhythmia is detected, the method continues to step S2, which determines whether the ventricular tachyarrhythmia is unstable or not. In the case of a stable tachyarrhythmia, no defibrillation shock needs to be applied, and the method returns to step S1 where a new investigation can be started. However, if the tachyarrhythmia is classified as unstable the method continues to step S3 where a suitable therapy, such as a defibrillation shock, is applied to the patient's heart. After therapy application, the method ends or preferably returns to step S1 for a new investigation cycle.

FIG. 7 is a flow diagram illustrating an additional step of the heart conditioning method of FIG. 6. The method starts in step S10, where intracardiac electric signals, i.e. electrocardiogram signals, are measured using different cardiac sensors or electrodes. The method then continues to step S1 of FIG. 6, where these electric signals are used for detecting the presence of a ventricular tachyarrhythmia. For example, the electrical signals could be used for detecting any high ventricular rate, PVC, irregular atrioventricular synchrony, etc. as previously described.

FIG. 8 is a schematic flow diagram illustrating the tachyarrhythmia classifying step of FIG. 6 in more detail. The method continues from step S1 of FIG. 6. In a next step S20, cardiogenic impedance representative of volumetric dynamics, such as blood filling dynamics, of the left and/or right ventricle of the heart is determined. The determined impedance signal is preferably an average impedance signal over multiple heart intervals. The method then continues to step S21, where the determined impedance signal is used for classifying the ventricular tachyarrhythmia as stable or unstable. If the tachyarrhythmia is classified as stable based on the impedance signal the method continues to step S1 of FIG. 6 otherwise it continues to step S3 of FIG. 6.

FIG. 9 is a flow diagram illustrating the impedance determining method of FIG. 8 in more detail. The method continues from step S1 of FIG. 6. In a next step S30, a current or voltage (pulse) signal is applied over two electrodes, preferably based on the detection of a ventricular tachyarrhythmia. A resulting voltage or current signal is then measured using two electrodes in step S31, of which preferably one and more preferably both, is/are different from the signal applying electrodes. The applied signal and the measured resulting signal are then processed in step S32 for generating a cardiogenic impedance signal representative of the ventricle volumetric dynamics. The processing preferably involves determining the impedance signal as an average signal over multiple time periods of different heart beats. The method then continues to step S11 of FIG. 8.

FIG. 10 is a flow diagram illustrating additional steps of the heart conditioning method. The method continues from step S10 of FIG. 8. In a next step S40, a mode-based measurement is performed for the purpose of determining a current body state, such as body posture, heart rate and/or body activity. In a next step S41, the measurement data collected in step S40 is used for selecting an impedance template from a set of multiple previously defined mode-specific impedance templates. Thus, such an impedance template associated with a current body posture, heart rate and/or body activity is selected in step S41. The determined (average) impedance signal is compared in a next step S42 with the template selected in step S41. The classification of the detected tachyarrhythmia is performed based on this signal-template comparison, preferably by performing a morphological signal comparison. The method then continues to step S11 of FIG. 8, where the tachyarrhythmia is classified as stable or unstable based on the (morphological) comparison.

FIG. 11 is a flow diagram illustrating additional steps of the conditioning method of FIG. 6 for generating different impedance templates. The method continues from step S1 of FIG. 1. In a next step S50, intracardiac impedance data is collected as previously described. In addition, a next step S51 simultaneously or at least in connection with the impedance data measurement performs mode-based measurements. This step basically corresponds to step S40 of FIG. 10 and is not further described. A next step S52 generates at least one impedance template based on the impedance data from step S50 and associates the template(s) with mode-specific parameters, such as body posture, heart rate and body activity at the time of impedance data collection. The steps S50 to S52 are preferably performed for different body postures, heart rates and/or body activities to form a set of different impedance templates that can be used in the tachyarrhythmia classification of the present invention. Such impedance templates can be collected both for normal heart condition, at stable tachyarrhythmia periods and at unstable tachyarrhythmia periods. The respective templates are preferably updated based on more recent collected impedance data over operation of the IMD in order to have as updated impedance templates as possible. The method then continues to step S1 of FIG. 6.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable medical device comprising:
   a tachyarrhythmia detector that detects a ventricular tachyarrhythmia in a heart of a subject based on an electrocardiogram signal measured for said heart;
   an impedance determining unit that determines a cardiogenic impedance signal representative of volumetric dynamics of at least one ventricle of said heart;
   a state defining unit that defines a current subject state of said subject; and
   a tachyarrhythmia classifier that classifies said ventricular tachyarrhythmia as a stable ventricular tachyarrhythmia or an unstable ventricular tachyarrhythmia based on said cardiogenic impedance signal;
   wherein said tachyarrhythmia classifier comprises:
   a template selector that selects a defined signal template from a set of multiple defined signal templates based on said current subject state defined by said state defining unit, each defined signal template being associated with a given subject state; and
   a comparator that compares said cardiogenic impedance signal with said defined signal template selected by said template selector.

2. The device according to claim 1, wherein said impedance determining unit comprises:
   a signal applier that applies, in response to said tachyarrhythmia detector detecting said ventricular tachyarrhythmia, a current signal or a voltage signal to at least a portion of said heart;
   a signal measurer that measures a resulting voltage signal or a resulting current signal over at least a portion of said heart; and
   a signal processor that determines said cardiogenic impedance signal based on said applied current or voltage signal and said measured resulting voltage or current signal.

3. The device according to claim 1, further comprising a lead input connected to said impedance determining unit and connectable to at least one intracardiac lead having at least one electrode for performing a quadropolar or tripolar impedance vector measurement.

4. The device according to claim 3, wherein said lead input is connectable to a right ventricle intracardiac lead having at least one electrode and a left ventricle intracardiac lead having at least one electrode, and wherein said impedance determining unit determines said cardiogenic impedance signal by using a quadropolar or tripolar impedance vector between said at least one electrode of said right ventricle intracardiac lead and said at least one electrode of said left ventricle intracardiac lead.

5. The device according to claim 3, wherein said lead input is connectable to a right atrium intracardiac lead having at least one electrode and a right ventricle intracardiac lead having at least one electrode, and wherein said impedance determining unit determines said cardiogenic impedance signal using a quadropolar or tripolar impedance vector between said at least one electrode of said right atrium intracardiac lead and said at least one electrode of said right ventricle intracardiac lead.

6. The device according to claim 1, wherein said impedance determining unit i) measures cardiogenic impedance during multiple time periods of different heart beats and ii) determines said cardiogenic impedance signal as an average of said cardiogenic impedance measured during different heart beats.

7. The device according to claim 1, wherein said tachyarrhythmia detector detects said ventricular tachyarrhythmia by detecting a presence of a premature ventricular contraction or irregular atrio-ventricular synchrony as determined by processing said measured electrocardiogram signal.

8. The device according to claim 1, wherein said tachyarrhythmia detector detects said ventricular tachyarrhythmia based on a heart rate of said heart determined from said electrocardiogram signal.

9. The device according to claim 1, wherein said tachyarrhythmia classifier is arranged for classifying said ventricular tachyarrhythmia as a stable ventricular tachyarrhythmia or an unstable ventricular tachyarrhythmia based on said comparison performed by said comparator.

10. The device according to claim 1, wherein said state defining unit is a heart rate unit that measures a heart rate of said subject, and wherein said template selector selects a defined signal template from said set of multiple defined signal templates based on said heart rate measured by said heart rate unit, each defined signal template being associated with a given heart rate interval.

11. The device according to claim 1, wherein said state defining unit is a posture unit determines a body posture of said subject, and wherein said template selector selects a defined signal template from said set of multiple defined signal templates based on said body posture determined by said posture unit, each defined signal template being associated with a given body posture.

12. The device according to claim 1, wherein said comparator performs a morphological comparison of said cardiogenic impedance signal and said defined signal template.

13. The device according to claim 1, wherein said impedance determining unit measures a cardiogenic impedance representative of volumetric dynamics of at least one ventricle of said heart during a period of no ventricular tachyarrhythmia, and wherein said implantable medical device further comprises a template unit that determines at least one of said defined signal templates based on said cardiogenic impedance measured by said impedance determining unit.

14. The device according to claim 13, wherein said template unit intermittently updates said defined signal templates based on cardiogenic impedances representative of volumetric dynamics of at least one ventricle of said heart measured by said impedance measuring unit during different periods of no ventricular tachyarrhythmia.

15. The device according to claim 1, wherein said impedance determining unit measures a cardiogenic impedance representative of volumetric dynamics of at least one ventricle of said heart during a period of stable ventricular tachyarrhythmia, and wherein said implantable medical device further comprises a template unit that determines at least one of said defined signal templates based on said cardiogenic impedance measured by said impedance determining unit.

16. A heart conditioning method comprising the steps of:
  detecting a ventricular tachyarrhythmia in a heart of a subject based on an electrocardiogram signal measured for said heart;
  determining a cardiogenic impedance signal representative of volumetric dynamics of at least one ventricle of said heart;
  defining a current subject state of said subject;
  selecting a defined signal template from a set of multiple defined signal templates based on said defined subject state, where each defined signal template is associated with a given subject state;
  comparing said cardiogenic impedance signal with said selected, defined signal template; and
  classifying said ventricular tachyarrhythmia as a stable ventricular tachyarrhythmia or an unstable ventricular tachyarrhythmia based on said comparing of said cardiogenic impedance signal and said selected defined signal template.

17. The method according to claim 16, wherein said determining step comprises determining, based on said detection of said ventricular tachyarrhythmia, said cardiogenic impedance signal.

18. The method according to claim 16, wherein said determining step comprises determining said cardiogenic impedance signal using a quadropolar or tripolar impedance vector.

19. The method according to claim 18, wherein said determining step comprises determining said cardiogenic impedance signal using a quadropolar or tripolar impedance vector between a left ventricle and a right ventricle of said heart.

20. The method according to claim 18, wherein said determining step comprises determining said cardiogenic impedance signal using a quadropolar or tripolar impedance vector between a right atrium and a right ventricle of said heart.

21. The method according to claim 16, wherein said determining step comprises the steps of:
  measuring cardiogenic impedance during multiple time periods of different heart beats; and
  determining said cardiogenic impedance signal as an average of said cardiogenic impedance measured during different heart beats.

22. The method according to claim 16, wherein said detecting step comprises the steps of:
  determining an electrocardiogram signal in said heart; and
  detecting said ventricular tachyarrhythmia by detecting a presence of a premature ventricular contraction or an irregular atrio-ventricular synchrony in said electrocardiogram signal.

23. The method according to claim 16, wherein said detecting step comprises the steps of:
  determining a heart rate of said heart based on said electrocardiogram signal; and
  detecting said ventricular tachyarrhythmia based on said determined heart rate.

24. The method according to claim 16, wherein said defining step comprises measuring a heart rate of said subject, and said selecting step comprises selecting a defined signal template from said set of multiple defined signal templates based on said measured heart rate, where each defined signal template is associated with a given heart rate interval.

25. The method according to claim 16, wherein said defining step comprises determining a body posture of said subject, and said selecting step comprises selecting a defined signal template from said set of multiple defined signal templates based on said determined body posture, where each defined signal template is associated with a given body posture.

26. The method according to claim 16, wherein said comparing step comprises performing a morphological comparison of said cardiogenic impedance signal and said selected defined signal template.

27. The method according to claim 16, further comprising the steps of:
  measuring a cardiogenic impedance representative of volumetric dynamics of at least one ventricle of said heart during a period of no ventricular tachyarrhythmia; and
  determining at least one of said defined signal templates based on said measured cardiogenic impedance.

28. The method according to claim 27, further comprising intermittently updating at least one of said defined signal templates based on measured cardiogenic impedances representative of volumetric dynamics of at least one ventricle of said heart during different periods of no ventricular tachyarrhythmia.

29. The method according to claim 16, further comprising the steps of:
  measuring a cardiogenic impedance representative of volumetric dynamics of at least one ventricle of said heart during a period of stable ventricular tachyarrhythmia; and
  determining at least one of said defined signal templates based on said measured cardiogenic impedance.

* * * * *